United States Patent
Šačkus et al.

(10) Patent No.: US 10,023,585 B2
(45) Date of Patent: Jul. 17, 2018

(54) PHOTOCHROMIC COMPOUNDS AND INTERMEDIATE COMPOUNDS FOR PRODUCTION THEREOF

(71) Applicant: KAUNAS UNIVERSITY OF TECHNOLOGY, Kaunas (LT)

(72) Inventors: Algirdas Šačkus, Kaunas (LT); Vytas Martynaitis, Kaunas (LT); Sonata Krikštolaitytė, Kaunas (LT); Greta Ragaitė, Kaunas (LT); Mikas Vengris, Vilnius (LT)

(73) Assignee: KAUNAS UNIVERSITY OF TECHNOLOGY, Kaunas (LT)

( * ) Notice: Subject to any disclaimer, the term of this patent is extended or adjusted under 35 U.S.C. 154(b) by 0 days.

(21) Appl. No.: 15/533,990

(22) PCT Filed: Nov. 30, 2015

(86) PCT No.: PCT/IB2015/059201
§ 371 (c)(1),
(2) Date: Jun. 7, 2017

(87) PCT Pub. No.: WO2016/092410
PCT Pub. Date: Jun. 16, 2016

(65) Prior Publication Data
US 2017/0355709 A1    Dec. 14, 2017

(30) Foreign Application Priority Data

Dec. 9, 2014    (LT) .................................... 2014 138

(51) Int. Cl.
| C07D 491/18 | (2006.01) |
| C07D 487/04 | (2006.01) |
| C07D 491/107 | (2006.01) |
| C07D 209/08 | (2006.01) |
| C09K 9/02 | (2006.01) |

(52) U.S. Cl.
CPC .......... *C07D 491/18* (2013.01); *C07D 209/08* (2013.01); *C07D 487/04* (2013.01); *C07D 491/107* (2013.01); *C09K 9/02* (2013.01); *C09K 2211/1022* (2013.01); *C09K 2211/1044* (2013.01)

(58) Field of Classification Search
CPC .................................................. C07D 491/18
See application file for complete search history.

(56) References Cited

U.S. PATENT DOCUMENTS

| 5,155,230 A | 10/1992 | Hibino et al. |
| 5,241,075 A | 8/1993 | Hibino et al. |
| 6,410,754 B1 | 6/2002 | Soula et al. |
| 8,252,209 B2 | 8/2012 | Raymo et al. |

FOREIGN PATENT DOCUMENTS

| EP | 0411884 A1 | 2/1991 |
| GB | 1270928 A | 4/1972 |
| JP | 2006249622 A | 9/2006 |
| LT | 6024 B | 4/2014 |
| WO | WO 2012/172093 A1 | 12/2012 |
| WO | WO 2014/035224 A1 | 3/2014 |
| WO | WO 2014/189348 A1 | 11/2014 |

OTHER PUBLICATIONS

English language Abstract of JP 2006249622 A (Sep. 21, 2006).
English language Abstract of LT 6024 B (Apr. 25, 2014).
Greta Ragaite et al., "Fast and stable light-driven molecular switch based on a 5a,13-methanoindolo[2,1-b][1,3]benzoxazepine ring system", Dyes and Pigments., vol. 113, Sep. 28, 2014 (Sep. 28, 2014), GB, pp. 546-553, XP055238572, ISSN: 0143-7208, DOI: 10.1016/j.dyepig.2014.09.006.
V. Malatesta: "Photodegradation of Organic Photochromes in Organic Photochromic and Thermochromic Compounds", vol. 2, Eds. J. C. Crano and R. J. Guglielmetti, Kluwer Academic/Plenum Publishers, New York, 1991, pp. 473.
R. Zemribo, J. Fotins and U. A. Holger Kubas et al.: "Photochromism of dihydroindolizines: part XIV. Synthesis and photophysical behavior of photochromic dihydroindolizine tripodal linkers toward anchoring sensitizers to semiconductor nanoparticles", J. Phys. Org. Chem., vol. 24, 2011, pp. 173-184.
T. B. Shrestha, J. Melin and Y. Liu et al.: "New insights in the photochromic spiro-dihydroindolizine/betaine-system", Photochem. Photobiol. Sci., vol. 7, 2008, pp. 1449-1456.
N. P. Gritsan, L. S. Klimenko, J. Photochem. Photobiol. A: Chem., vol. 70, 1993, pp. 103-117.
C. D. Gabbutt, B. M. Heron, S. B. Kolla et al.: "Ring contraction during the 6p-electrocyclisation of naphthopyran valence tautomers", Org Biomol Chem, vol. 6, 2008, pp. 3096-3104.

(Continued)

*Primary Examiner* — Shawquia Jackson
(74) *Attorney, Agent, or Firm* — Hershkovitz & Associates, PLLC; Abe Hershkovitz (57) ABSTRACT

The invention covers new bicyclic bridged [1,3]oksazepine derivatives of the general formula (I) and (II):

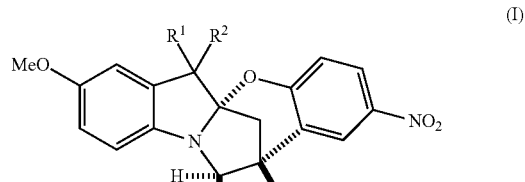

(I)

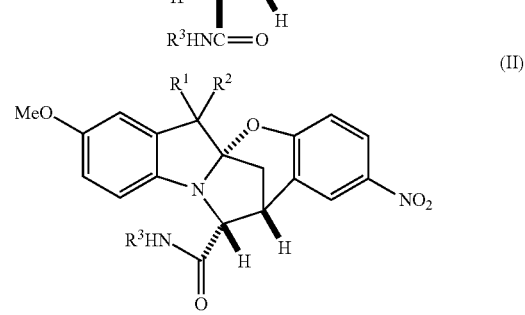

(II)

which exhibit enhanced photochromic properties as compared with known spiropyrans and can be used as molecular photoswitches. The method of production of new compounds and intermediates for preparation thereof are disclosed.

20 Claims, 1 Drawing Sheet

(56) References Cited

OTHER PUBLICATIONS

V. I. Minkin: "Photoswitchable molecular systems based on spiropyrans and spirooxazines" in "Molecular switches", vol. 1-2, 2011, Wiley-VCH, pp. 37-80.
R. C. Bertelson: "Organic Photochromic and Thermochromic Compounds", Eds. J. C. Crano, R. J. Guglielmetti, vol. 1-2, 1999, Plenum Press, pp. 11-84.
T. Stafforst, D. Hilvert: "Kinetic characterization of spiropyrans in aqueous media", Chem. Commun., 2009, pp. 287-288.
International Search Report of PCT/IB2015/052676 dated Aug. 26, 2015.

PHOTOCHROMIC COMPOUNDS AND INTERMEDIATE COMPOUNDS FOR PRODUCTION THEREOF

TECHNICAL FIELD

The present invention is concerned with new bycyclic bridged [1,3]oxazepine derivatives, which possess enhanced photochromic properties and can be used as molecular photoswitches.

The invention also discloses method of production of said new photochromic compounds and intermediates for their preparation.

BACKGROUND ART

Photochromic compounds of various classes are known: indoline spiropyrans, indoline spirooxazines, benzo- and naphthopyrans, fulgides, diarylethenes, quinones, perimidinespirocyclohexadienones [V. Malatesta, Photodegradation of Organic Photochromes In Organic Photochromic and Thermochromic Compounds. Vol. 2 Eds. J. C. Crano and R. J. Guglielmetti. Kluwer Academic/Plenum Publishers, New York, 1991, 473 pp.], indolo[2,1-b][1,3]benzoxazines. Exposition the solutions of spiropyrans and spirooxazines to UV irradiation brakes C—O bond and coloured merocyanines form, which revert back to the initial state due to the thermal movement of molecules or after irradiation with visuable light during micro- and miliseconds. Known photochromic compounds—indolino spiropyrans, for example, are described in patents EP0411884A1, GB1270928A, JP2006249622A, U.S. Pat. Nos. 5,155,230, 5,241,075 and others. Dihydroindolines, similarly to indolino spiropyrans, after irradiation with UV are transfered to coloured form and revert back to the initial state thermaly, but the livetime of coloured form is longer comparing with indolinespiropyrans, and it is up to hundreds of milliseconds, minutes or even hours. [WO2012172093; R. Zemribo, J. Fotins, U. A. Holger Kubas et al., Photochromism of dihydroindolizines: part XIV. Synthesis and photophysical behavior of photochromic dihydroindolizine tripodal linkers toward anchoring sensitizers to semiconductor nanoparticles. J. Phys. Org. Chem. 2011, 24 173-184; T. B. Shrestha, J. Melin. Y. Liu, et al., New insights in the photochromic spiro-dihydroindolizine/betaine-system. Photochem. Photobiol. Sci., 2008, 7, 1449-1456]. Another known class of photochromic compounds—quinones also do not demonstrate very fast interchange of uncoloured-coloured forms ant it takes from few till hundreds of microseconds [N. P. Gritsan, L. S. Klimenko. J. Photochem. Photobiol. A: Chem. 1993, 70, 103-117].

Perimidinecyclohexadienones are characterized by extremely long lifetime of coloured form, which reaches few days due to Z-E configurational exchange, similarly to E-Z in merocyanines. Relatively recently discovered photochromic compounds benzo- and naphthopyrans are not sufficient photostable. Due to the action of UV irradiation pyrane ring is transformed to furane ring and initial compound loses photochromic properties. [C. D. Gabbutt, B. M. Heron, S. B. Kolla, et al. Ring contraction during the 6p-electrocyclisation of naphthopyran valence tautomers. Org Biomol Chem 2008; 6:3096-3104; U.S. Pat. No. 6,410,754B1]. Fulgides and fulgimides are characterized by electrocyclization reaction, occurring when they are exposed to UV irradiation, when coloured 1,3-cyclohexadiene fragment possessing compounds are formed. The latter are thermally stable and can be transferred into the initial state only after irradiation with visible light. Diarylethenes, which also are thermally stable, act similarly.

Some of the newest classes of photochromic compounds—indole[2,1-b][1,3]benzoxazines, have a thermally unstable colored form, but they are much faster than the indoline spiropyrans and lifetimes thereof are shorter than of indoline spiropyrans [U.S. Pat. No. 8,252,209]. A new class of photochromic compounds, 6-nitro-1,3,3',4-tetrahydrospiro[chromen-2,2'-indoles], is described in Lithuanian patent LT6024 (WO2014/035244), which coloured form lifetime is only 22-41 ns.

When indoline spiropyrans are exposed to ultraviolet irradiation, breaking of pyrane ring occurs and coloured merocyanine form appears [V. I. Minkin, Photoswitchable molecular systems based on spiropyrans and spirooxazines, 37-80 pp. In Molecular switches/edited by B. L. Feringa and W. R. Browne. Weinheim, Wiley-VCH, 2011, Vol. 1-2; Spiropyrans. R. C. Bertelson, 11-84 pp. In Organic Photochromic and Thermochromic Compounds, Vol. 1-2, Eds. J. C. Crano, R. J. Guglielmetti, Plenum Press. New York and London, 1999, Vol. 1-2.]. Thermal transformation of the formed merocyanine to spiropyran is retarded significantly due to trans-cis reisomerization stage, which takes place when coloured form returns to initial spiropyran form, and this takes miliseconds.

spiropyran     cis-merocyanine     trans-merocyanine Coloured form generation from indolino spiropyrans is relatively fast, but due to thermo- and photochemical degradation they stand less cycles and also are not resistant to air oxygen [V. Malatesta, Photodegradation of Organic Photochromes In Organic Photochromic and Thermochromic Compounds. Vol. 2 Eds. J. C. Crano and R. J. Guglielmetti. Kluwer Academic/Plenum Publishers, New York, 1991, 473 pp.]. Besides, spiropyrans in merocyanine form are easily hydrolysable [Stafforst, T., and Hilvert, D. Kinetic characterization of spiropyrans in aqueous media. *Chem. Commun.* 2009, 287-288].

A new class of photochromic compounds, namely 6-nitro-1,3,3',4-tetrahydrospiro[chromen-2,2'-indoles], possessing carbon skeleton of indoline spiropyrans, where double bond in pyrane ring is hydrogenated, is described in the above-mentioned Lithuanian patent LT6024 (WO2014/035244).

A ⇌ B

After irradiation of such 1',3,3',4-tetrahydrospiro[chromen-2,2'-indoles] (A) with UV radiation a colored 4-nitrophenolate fragment (B) forms, which due to molecular thermal movement returns into the initial state during few tens of nanoseconds. This is because in the absence of double bond it is not necessary to isomerize from trans- to cis-isomeric forms. However compound A is very sensitive for alkaline medium.

Immediate substitution of phenolate at asymmetric carbon atom appears, and coloured compound C possessing 4-nitrophenol fragment forms, if any amount of hydroxide ions is present in the solution, and photochromic effect disappears.

A → C (KOH or Na₂CO₃)

Therefore, it is important to have photochromic compounds that respond quicker and will not lose their photochromic properties in alkaline solution.

DISCLOSURE OF THE INVENTION

The goal of present invention is to get new photochromic compounds, that act by openind and closing of 3,4-dihydropyrane ring in methanobenz[f][1,3]oxazepino[3,2-a]indoles, which rate of opening/closing be higher than of known photochroms, and be active in both neutral and alkaline mediums.

To achieve this goal the compounds of general formulae (I) and (II) are proposed (I)

(II)

wherein
$R^1$ and $R^2$ each independently are methyl, ethyl or are part of spirocycle: —(CH$_2$)$_4$—; —(CH$_2$)$_5$—;
$R^3$ is $C_1$-$C_6$-alkyl, ω-functionalized alkyl, benzyl, phenyl, allyl.

Here ω-functionalized alkyl is having polymerizable groups (vinyl, acrylate, epoxy) or tiol groups, capable of connecting to various substrates.

More specifically, the present invention covers compounds of the general formula (I) or (II) wherein $R^1$ and $R^2$ are methyls and $R^3$ is ethyl or benzyl.

Preferred target compounds of present invention are:
(5aR*,12R*,13S*)-N-Ethyl-6,6,8-trimethyl-2-nitro-12,13-dihydro-6H-5a,13-methanoindolo[2,1-b][1,3]benzoxazepine-12-carboxamide (6a);

(5aR*,12S*,13S*)-N-Ethyl-6,6,8-trimethyl-2-nitro-12,13-dihydro-6H-5a,13-methanoindolo[2,1-b][1,3]benzoxazepine-12-carboxamide (7);
(5aR*,12R*,13S*)-N-Benzyl-6,6,8-trimethyl-2-nitro-12,13-dihydro-6H-5a,13-methanoindolo[2,1-b][1,3]benzoxazepine-12-carboxamide (6b).

The target compounds of the present invention are characterized by photochromic properties. They can be used as photochromic switches.

Another object of the invention are compounds of general formula (5), (5)

wherein R³ is ethyl or benzyl, and which compounds are intermediates for obtaining photochromic compounds of present invention.

Yet another object of present invention are compounds of general formula (4), which are used in synthesis of compounds (5):

(4)

wherein R³ is ethyl or benzyl.

Another one object of present invention is compound of formula (3), which is used in synthesis of compound (4):

(3)

One more object of present invention is 3H-indolium salt of formula (2), which is used in synthesis of compound of formula (3):

(2)

DETAILED DESCRIPTION OF THE INVENTION

New class of photochromic compounds is developed, comprising derivatives of general formula (I) and (II) cis- and trans-methanobenz[f][1,3]oxazepino[3,2-a]indole derivatives I and II

III          IV

These derivatives have skeleton of 1',3,3',4-tetrahydrospiro[chromen-2,2'-indole]formed from indole (A) and chromane(B) heterocyclic systems, similarly to recently published fotochromic compounds, 1',3',3'-trimethyl-6-nitro-1',3,3',4-tetrahydrospiro[chromen-2,2'-indoles] III and IV.

However, compounds of present invention are bearing an additional C—C bond (shown above in bold), which reduces conformational lability of pyrane ring.

pound of formula (3) was obtained by cyclization of 3H-indolium salt, and the latter salt of formula (2) was obtained by alkylation of 2,3,3a-trimethyl-5-methoxy-3H-indole by 2-chloroacetamide. For skilled specialists in organic synthesis it is understandable, how to prepare other compounds of present invention.

It was found by the treatments that, that when solutions of compounds proposed in the present invention were irradiated with monochromatic ultraviolet light (for example,

The structure of compounds of present invention was found to be pecular in that under the action of ultraviolet radiation on compound type I, breaking of C—O bond in 3,4-dihydro[2H]pyrane ring occurs, generating coloured zwitterion V, possessing coloured 4-nitrophenolate fragment. This fragment is connected by only one bond, being able to turn about it. Meanwhile, when known high speed photochroms A are triggered by UV irradiation, zwitterionic compound B generates, in which 4-nitrophenolate moiety is connected with indolium moiety through three single bonds around which rotation is possible. The reduction of degree of freedom due to possible rotation around single C—C bonds in the structure V (1 bond), comparing with structure B (3 bonds), is advantageous in that dihydropyrane ring restors quicker than 5 ns, and compound V returns to the initial structure I.

As mentioned above, the invention includes novel intermediates, necessary to obtain the target compounds.

To the knowledge of the authors, intermediates (2) (3) (4) (5) are not described, though they may be prepared by known synthesis methods. Intermediates of general formula (5) were obtained by condensing the compounds of the general formula (4), e.g. with 2-hydroxy-5-nitrobenzaldehyde. Compounds of the general formula (4) were prepared by alkylation of 7-methoxy-9,9,9a-trimethyl-9H-imidazo[1,2-a]indol-2-ona with iodoethane or benzylchloride. Com- Nd:YAG laser (EKSPLA NL30); third harmonic; wavelength 355 nm; pulse duration—5 ns; pulse energy 3 mJ) heterolytic breaking of bond connecting chiral center (marked by asterix) with oxygen atom occurrs yielding formation of cwitterionic compound, comprising the conformationally constrained chain of two carbon atoms connecting fragments of 3H-indolium cation and coloured 4-nitrophenolate anion. After switching irradiation off the coloured form of compound thermally returns to the initial colourless state, after connection of oxygen atom of phenolate anion to α-carbon atom of indole ring system. Compounds of the present invention methanobenz[f][1,3]oxazepino[3,2-a]indoles are characterized by higher total speed of cycle closing/opening, besides they operate in oxygen environment as well. cis-Methanobenz[f][1,3]oxazepino[3,2-a] indoles are less sensitive to pH of environment, especially for alkaline medium, while 6-nitro-1',3,3',4-tetrahydrospiro [chromen-2,2'-indoles] are extremely sensitive to the bases. Compounds described in present patent application were synthesized by recyclization reaction of corresponding indolino spiropyrane, when treated with potassium hydroxyde in ethanol under reflux.

Said methanobenz[f][1,3]oxazepino[3,2-a]indoles are obtainable according to general scheme below:

1-7: $R^1 = R^2 = Me$; $R^3 = Et, Bn$; $X = halogen$.

MODES FOR CARRYING OUT THE INVENTION

Information on examples of real embodiments is provided below, disclosing the modes of preparation compounds of present invention and properties thereof. This information is provided for the illustrative purpose and is not limiting the scope of present invention.

Example 1

5-Methoxy-2,3,3-trimethyl-3H-indolium chloride (initial compound)

5-Methoxy-2,3,3-trimethyl-3H-indole 12 g (0,063 mol) was dissolved in toluene (20 ml), condenser was attached to the flask and acethyl chloride 9 ml (p=1.104 g/Ml, 9,94 g) was added dropwise. After cooling the mixture to ambient temperature, the mixture was stored at 5° C. for 12 h. Formed crystals were filtered, washed with acetone and cold ether. Yield is 6.6 g of indolium chloride (46.12%) as yellowish crystals. M.p. 201-203° C. $^1H$ NMR (400 MHz, DMSO-$D_6$): δ 1.45 (s, 6H, 2×$CH_3$), 2.62 (s, 3H, 2-$CH_3$), 3.82 (s, 3H, 5-$OCH_3$), 7.02 (dd, J=8.8 Hz, J=2.4 Hz, 1H, 6-H), 7.37 (d, J=2.4 Hz, 1H, 4-H), 7.54 (d, J=8.4 Hz, 1H, 7-H). $^{13}C$ BMR (100 MHz, DMSO-$D_6$): δ 14.3, 22.0 (2×C), 53.8, 55.9, 109.4, 113.9, 117.2, 134.9, 145.3, 159.7, 193.0. IR (KBr), ν ($cm^{-1}$): 3134 (N—H), 3021, 2973, 1623, 1479, 1404, 1289, 1022, 797.

Example 2

1-Carbamoylmethyl-5-methoxy-2,3,3-trimethyl [3H]indolium chloride (Intermediate Compound 2)

5-Methoxy-2,3,3-trimethyl-3H-indolium chloride (6 g, 0.026 mol) obtained according to Example 1 was dissolved in minimal amount of water, neutralized with sodium carbonate and extracted with diethyl ether (2×30 ml). Combined extract was dried over anhydrous sodium sulfate and solvent was removed on rotavapor. To the obtained residue (4.8 g, 0,025 mol) α-chloroacetamide (2.6 g, 0.027 mol) was added and the mixture was heated at 140° C. for 2 h in o-xylene (7 ml) with condenser. After cooling the formed crystals were filtered and washed with cold ether. After recrystallization from ethanol 5 g of product was obtained, yield 69.7% of dark brown crystals, m.p. 240-242° C. $^1H$ NMR (400 MHz, DMSO-$d_6$): δ 1.54 (s, 6H, 2×$CH_3$), 2.73 (s, 3H, $CH_3$), 3.85 (s, 3H, O—$CH_3$), 5.36 (s, 2H, $CH_2CO$), 7.14 (dd, J=8.8 Hz, J=2.4 Hz, 1H, 6-H), 7.51 (d, J=2.4 Hz, 1H, 4-H), 7.79-7.81 (m, 2H, 7-H, ½$NH_2$), 8.51 (pl.s, 1H, % $NH_2$). $^{13}C$ BMR (100 MMHz, DMSO-$D_6$): δ 14.4, 22.6 (2×C), 50.1, 54.5, 56.6, 109.9, 114.9, 116.3, 135.2, 143.9, 161.1, 165.1, 196.4. IR (KBr), ν ($cm^{-1}$): 3290 (N—H), 3097, 2977, 1689 (C=O), 1298, 1030, 833.

Example 3

7-Methoxy-9,9,9a-trimethyl-9,9a-dihydro-1H-imidazo[1,2-a]indol-2(3H)-one (Intermediate Compound 3)

1-Carbamoylmethyl-5-methoxy-2,3,3-trimethyl-3H-indolium chloride (5 g, 0,018 mol), that was synthesized according method of example 2, was dissolved in minimal amount of water, neutralized with sodium carbonate and extracted with diethyl ether (2×25 ml). Etheral extracts were combined, dried over anhydrous sodium sulphate and solvent was evaporated on rotavapor. To the obtained neutralized mixture (5 g, 0.02 mmol) ethanol (20 ml) and glacial acetic acid (9.2 ml) were added and the mixture was heated at 100° C. for 1 h. After cooling the mixture it was poured into water (50 ml) and neutalized with $Na_2CO_3$, till white crystals start forming. The substance was filtered, washed with water and re-crystallized from ethanol. Yield of product 2.5 g (50%) as of white crystals, m.p. 209-211° C. $^1H$ NMR (400 MHz, $CDCl_3$): δ 1.17 (s, 3H, $CH_3$), 1.36 (s, 3H, $CH_3$), 1.50 (s, 3H, $CH_3$), 3.76 (s, 3H, O—$CH_3$), 3.77 (AB-q, J=16.4 Hz, 2H, $CH_2$), 6.62 (d, J=2.8 Hz, 1H, 4-H), 6.64 (d, J=8.8 Hz, 1H, 7-H), 6.70 (dd, J=8.8 Hz, J=2.4 Hz, 1H, 6-H), 7.86 (pl. s, 1H, NH). $^{13}C$ BMR (100 MHz, $CDCl_3$): δ 21.2, 22.3, 27.5, 47.0, 55.8, 55.9, 92.0, 109.1, 112.8, 113.3, 140.2, 144.3, 155.9, 174.9 (C=O). IR (KBr, $cm^{-1}$): 3333 (N—H), 3056, 2975, 1700 (C=O). MS m/z (%): 247 ($M+H^+$, 100).

Example 4

1-Ethyl-7-methoxy-9,9,9a-trimethyl-9,9a-dihydro-1H-imidazo[1,2-a]indol-2(3H)-one (Intermediate Compound 4a)

7-Methoxy-9,9,9a-trimethyl-9,9a-dihydro-1H-imidazo[1,2-a]indol-2(3H)-one 2,5 g (0.01 mol), that was synthesized according to method described for example 3, was dissolved in dimethylformamide (25 ml) and to the solution freshly powdered KOH (0,85 g) was added. After dissolution of alkali, iodoethane (2.45 ml) was added dropwise and stirring was continued for 3 h. The mixture was poured into water and extracted with ether (3×20 ml). Etheral extracts were combined, washed with 5% solution of HCl. Neutralized with $Na_2CO_3$ solution, dried over anhydrous sodium sulphate and solvent was evaporated on rotavapor. Yield of product 2.3 g (82.7%) as yellowish resinous substance. $^1H$ NMR (400 MHz, $CDCl_3$): δ 1.04 (s, 3H, $CH_3$), 1.29 (t, J=7.2 Hz, 3H, $CH_2CH_3$), 1.40 (s, 3H, $CH_3$), 1.47 (s, 3H, $CH_3$), 2.98-3.07 (m, 1H, ½$CH_2CH_3$), 3.63-3.72 (m, 1H, % $CH_2CH_3$), 3.76 (s, 3H, $OCH_3$), 3.83 (AB-q, J=15.2 Hz, 2H, CO—$CH_2$), 6.59 (d, J=2.8 Hz, 1H, 4-H), 6.70-6.71 (m, 2H, Ar—H). $^{13}C$ NMR (100 MHz, $CDCl_3$): δ 14.33, 23.07, 24.11, 27.02, 29.19, 37.23, 50.06, 55.84, 92.69, 108.99, 113.01, 115.36, 142.23, 142.99, 156.05, 171.22 (C=O). IR (KBr), ν ($cm^{-1}$): 3029, 2984, 1703 (C=O), 1491, 1273, 1014, 816.

Example 5

1-Benzyl-7-methoxy-9,9,9a-trimethyl-9,9a-dihydro-1H-imidazo[1,2-a]indol-2(3H)-one (Intermediate Compound 4b)

7-Methoxy-9,9,9a-trimethyl-9,9a-dihydro-1H-imidazo[1,2-a]indol-2(3H)-one 2,0 g (0,008 mol), that was synthesized according to method described for example 3, was dissolved in dimethylformamide (18 mL), and to the solution 0,7 g (0.12 mol) freshly grounded KOH was added. After dissolution of alkali 3.08 benzyl chloride was added dropwise 2.8 mL (0,024 mol, p=1.100 g/Ml, 3.08 g) and stirring continued for 3 hrs at room temperature. The mixture was poured into water and extracted with ether (3×20 mL). Combined extract was washed with 5% HCl solution and neutralized with $Na_2CO_3$ solution. Solvent was dried over anhydrous sodium sulphate and evaporated with rotavapor. Obtained resin was purified by column chromatography (eluent: hexane/acetone 3:1). Yield of product 1.4 g (51.8%) as slightly orange crystals, m.p. 122-123° C. $^1H$ NMR (400 MHz, $CDCl_3$): δ 1.01 (s, 3H, 9a-$CH_3$, 1.25 (s, 3H, 9-$CH_3$), 1.37 (s, 3H, 9-$CH_3$), 3.73 (AB-d, J=15.2 Hz, 1H, ½$CH_2CO$), 3.73 (s, 3H, 7-$OCH_3$), 4.14 (dd, J=15.5 Hz, J=5.8 Hz, 2H, $CH_2$-Ph), 4.95 (AB-d, J=15.6 Hz, 1H, ½$CH_2CO$), 6.55 (d, J=2.5 Hz, 1H, 8-H), 6.69 (dd, J=8.4 Hz, J=2.5 Hz, 1H, 6-H), 6.74 (d, J=8.4 Hz, 1H, 5-H), 7.21-7.28 (m, 5H, Ar—H). $^{13}C$ NMR (100 MHz, $CDCl_3$): δ 23.3, 23.9, 28.7, 45.4, 50.1, 55.7, 55.8, 93.1, 108.9, 113.0, 115.6, 127.5, 127.6 (2×C), 128.7 (2×C), 137.7, 142.1, 143.2, 156.2, 172.1 (C=O). IR (KBr), ν (cm⁻): 3023, 2969, 1706 (C=O), 1493, 1278, 1027, 730.

Example 6

N-Ethyl-2-(5'-methoxy-3',3'-dimethyl-6-nitrospiro[chromen-2,2'-indolo]-1'(3'H)-yl)acetamide (Intermediate Compound 5a)

1-Ethyl-7-methoxy-9,9,9a-trimethyl-9,9a-dihydro-1H-imidazo[1,2-a]indol-2(3H)-one 2,5 g (0.009 mol), that was synthesized according method described for example 4, and 2-hydroxy-5-nitrobenzaldehyde 1.52 g (0.009 mol) were added to glacial acetic acid (20 mL) and heated at 100° C. for 3 hrs. After reaction completion the mixture was poured into 5% sodium acetate solution (250 mL) and extracted with ethyl acetate (2×30 ml). Combined extract was dried over anhydrous sodium sulfate and solvent was removed on rotavapor. Obtained resin was purified by column chromatography (eluent: hexane/acetone 3:1). Yield of product 1.3 g (33.8%) as violet amorphous substance. M.p. 95-96° C. $^1H$ NMR (400 MHz, $CDCl_3$): δ 1.09 (t, J=7.2 Hz, 3H, $CH_2\underline{CH_3}$), 1.26 (s, 3H, 3'-$CH_3$), 1.3 (s, 3H, 3'-$CH_3$), 3.25-3.34 (m, 2H, $\underline{CH_2}CH_3$), 3.59 (AB-d, J=17.6 Hz, 1H, ½$\underline{CH_2}CO$), 3.80 (s, 3H, 5'-$OCH_3$), 3.87 (AB-d, J=17.6 Hz, 1H, ½ $\underline{CH_2}CO$), 5.83 (d, J=10.4 Hz, 1H, $\underline{CH}$=CH), 6.43 (d, J=8.4 Hz, 1H, 7'-H), 6.49 (t, J=5.2 Hz, 1H, NH), 6.72 (dd, J=8.4 Hz, J=2.8 Hz, 1H, 6'-H), 6.75-6.78 (m, 2H, 4-H, 4'-H), 6.94 (d, J=10.4 Hz, 1H, CH=$\underline{CH}$), 8.00 (d, J=2.8 Hz, 1H, 7-H), 8.03 (dd, J=8.8 Hz, J=2.8 Hz, 1H, 5-H). $^{13}C$ NMR (100 MHz, $CDCl_3$): δ 15.0, 20.1, 26.1, 27.0, 34.3, 48.8, 52.9, 56.0, 106.6 (spiro-C), 108.3, 110.0, 111.7, 115.6, 118.3, 120.4, 123.1, 126.3, 129.4, 137.8, 140.0, 141.5, 155.4, 158.8, 169.3 (C=O). IR (KBr), ν ($cm^{-1}$): 3403 (N—H), 3065, 2966, 1666 (C=O), 1520, 1481, 1337, 1273, 1089, 951.

Example 7

N-Benzyl-2-(5'-methoxy-3',3'-dimethyl-6-nitrospiro[chromen-2,2'-indolo]-1'(3'H)-yl)acetamide (Intermediate Compound 5b)

1-Benzyl-7-methoxy-9,9,9a-trimethyl-9,9a-dihydro-1H-imidazo[1,2-a]indol-2(3H)-one 1.0 g (0.003 mol), that was synthesized according method described for example 5, and 2-hydroxy-5-nitrobenzaldehyde (0.5 g, 0.003 mol) were added to glacial acetic acid (10 mL) and heated at 100° C. for 3 hrs. After reaction completion the mixture was poured into 5% sodium acetate solution (100 mL) and extracted with ethyl acetate (2×30 ml). Combined extract was dried over anhydrous sodium sulfate and solvent was removed on rotavapor. Obtained resin was purified by column chromatography (eluent: hexane/acetone 3:1). Yield of product 0.41 g (28.7%) as violet amorphous substance. M.p. 84-85° C. $^1$H NMR (400 MHz, CDCl$_3$): δ 1.18 (s, 3H, 3'-CH$_3$), 1.27 (s, 3H, 3'-CH$_3$), 3.71 (AB-d, J=17.6 Hz, 1H, ½CH$_2$CO), 3.80 (s, 3H, 5'-OCH$_3$), 3.91, (AB-d, J=17.6 Hz, 1H, ½CH$_2$CO), 4.45 (d, J=5.6 Hz, 2H, CH$_2$-Ph), 5.76 (d, J=10.2 Hz, 1H, CH=CH), 6.45 (d, J=8.0 Hz, 1H, 4-H), 6.60 (d, J=8.4 Hz, 1H, 6'-H), 6.71 (dd, J=8.4 Hz, J=2.4 Hz, 1H, 7'-H), 6.74 (d, J=2.4 Hz, 1H, 4'-H), 6.83 (t, J=5.8 Hz, 1H, NH), 6.92 (d, J=10.2 Hz, 1H, CH=CH), 7.14-7.17 (m, 2H, Ar—H), 7.27-7.29 (m, 3H, Ar—H), 7.96-7.80 (m, 2H, 5-H, 7-H). $^{13}$C NMR (100 MHz, CDCl$_3$): δ 20.14, 26.10, 43.43, 48.75, 52.97, 56.06, 106.65 (spiro-C), 108.23, 110.06, 111.79, 115.61, 118.29, 120.51, 123.03, 126.31, 127.57 (2×C), 127.72, 128.87 (2×C), 129.41, 137.66, 138.0, 139.84, 141.58, 155.38, 158.66, 169.49 (C=O). IR (KBr), ν (cm$^{-1}$): 3395 (N—H), 3030, 2930, 1671 (C=O), 1519, 1494, 1481, 1337, 1272, 1089, 951.

Example 8

(5aR*,12S*,13S*)- and (5aR*,12R*,13S*)-N-Ethyl-8-methoxy-6,6-dimethyl-2-nitro-12,13-dihydro-6H-5a,13-methanoindolo[2,1-b][1,3]benzoxazepino-12-carboxamides (Target Compounds 6a, 7)

Spirocompound 5a (1 g, 0.002 mol), that was synthesized according to method described in example 6, was dissolved in ethanol (30 mL), fine grounded potassium hydroxyde (0.34 g, 0.006 mol) was added and the mixture was refluxed for 2 hrs. After reaction completion the most of solvent was removed on rotavapor, and to the residue water was added dropwise till solution became turbid. The mixture was hold at 5° C. for 10 hrs. Formed crystals were filtered, washed with small amount of cold ether, and recrystallized from ethanol. Filtrate was extracted with ethyl acetate (2×30 ml), combined extract was dried over anhydrous sodium sulfate and solvent was removed on rotavapor. Residue was purified by column chromatography (eluent: hexane/acetone 5:1). Obtained product was recrystallized from ethanol.

Cis-isomer (6a)

Yield 10.4%, yellow crystals, m.p. 241-242° C. $^1$H NMR (400 MHz, CDCl$_3$): δ 0.61 (t, J=7.2 Hz, 3H, CH$_2$CH$_3$), 1.48 (s, 3H, 6-CH$_3$), 1.50 (s, 3H, 6-CH$_3$), 2.16 (d, J=11.6 Hz, 1H, 14-Ha), 2.20 (dd, J=11.6 Hz, J=3.6 Hz, 1H, 14-H$_b$), 2.81-2.91 (m, 1H, ½CH$_2$CH$_3$), 3.12-3.23 (m, 1H, ½CH$_2$CH$_3$), 3.78 (s, 3H, 8-OCH$_3$), 3.80 (t, J=3.6 Hz, 1H, 13-H), 3.88 (d, J=4.8 Hz, 1H, 12-H), 6.43 (d, J=9.2 Hz, 1H, Ar—H), 6.66-6.69 (m, 2H, Ar—H), 6.89-6.92 (m, 2H, Ar—H, NH), 7.98 (d, J=2.8 Hz, 1H, 1-H), 8.07 (dd, J=9.2 Hz, J=2.8 Hz, 1H, 3-H). $^{13}$C NMR (100 MHz, CDCl$_3$): δ 14.7, 23.11, 26.6, 32.9, 33.7, 42.4, 45.5, 56.0, 78.2, 109.6, 111.1, 111.5, 113.1, 116.3, 124.7, 125.1, 125.9, 139.8, 141.4, 142.4, 156.0, 158.4, 169.5 (C=O). IR (KBr), ν (cm$^{-1}$): 3288 (N—H), 3071, 2982, 1652 (C=O), 1513, 1344, 1269, 1090, 816.

Trans-isomer (7)

Yield 2.5%, yellowish crystals, m.p. 184-185° C. $^1$H NMR (400 MHz, CDCl$_3$): δ 1.09 (t, J=7.2 Hz, 3H, CH$_2$CH$_3$), 1.37 (s, 3H, 6-CH$_3$), 1.60 (s, 3H, 6-CH$_3$), 2.05 (d, J=11.6 Hz, 1H, 14-Ha), 2.69 (dd, J=11.6 Hz, J=4.0 Hz, 1H, 14-H$_b$), 3.24-3.35 (m, 2H, CH$_2$CH$_3$), 3.75 (s, 3H, 8-OCH$_3$), 3.77 (d, J=4.0 Hz, 1H, 13-H), 4.31 (s, 1H, 12-H), 5.97 (t, J=5.2 Hz, 1H, NH), 6.25 (d, J=8.4 Hz, 1H, 10-H), 6.59 (dd, J=8.4 Hz, J=2.4 Hz, 1H, 9-H), 6.75 (d, J=2.4 Hz, 1H, 7-H), 6.79 (d, J=9.2 Hz, 1H, 4-H), 8.03 (dd, J=8.8 Hz, J=2.8 Hz, 1H, 3-H), 8.16 (d, J=2.8 Hz, 1H, 1-H). IR (KBr), ν (cm$^{-1}$): 3298 (N—H), 3082, 2970, 1650 (C=O), 1510, 1496, 1338, 1268, 1086, 917.

Example 9

(5aR*,12S*,13S*)-N-Benzyl-8-methoxy-6,6-dimethyl-2-nitro-12,13-dihydro-6H-5a,13-methanoindolo[2,1-b][1,3]benzoxazepino-12-carboxamide (Target Compound 6b)

Spirocompound 5b 0.385 g (0.8 mmol), that was synthesized according to method described in example 7 was dissolved in ethanol (10 mL), fine ground potassium hydroxide (0.13 g, 2.4 mmol) was added and the mixture was refluxed for 2 hrs. After reaction completion the most of solvent was removed on rotavapor and water was added dropwise till solution became turbid. The mixture was hold at 5° C. for 10 hrs. Formed crystals were filtered, washed with small amount of cold ether and recrystallized from ethanol. Yield 23.4% as yellow crystals. M.p. 218-219° C. $^1$H NMR (400 MHz, CDCl$_3$): δ 1.46 (s, 6H, 2×6-CH$_3$), 2.13 (d, J=11.6 Hz, 1H, 14-Ha), 2.21 (dd, J=11.6 Hz, J=4.0 Hz, 1H, 14-H$_b$), 3.78 (s, 3H, 8-OCH$_3$), 3.82 (t, J=4.0 Hz, 1H, 13-H), 3.93-3.97 (m, 2H, ½CH$_2$-Ph, 12-H), 4.51 (dd, J=14.8 Hz, J=8.0 Hz, 1H, ½CH$_2$-Ph), 6.46 (d, J=9.2 Hz, 1H, 4-H), 6.68-6.70 (m, 2H, Ar—H), 6.73-6.75 (m, 2H, Ar—H), 6.79 (d, J=8.8 Hz, 1H, Ar—H), 7.10-7.16 (m, 3H, Ar—H), 7.28-7.31 (m, 1H, NH), 7.93 (d, J=2.8 Hz, 1H, 1-H), 7.97 (dd, J=9.2 Hz, J=2.8 Hz, 1H, 3-H). $^{13}$C NMR (100 MHz, CDCl$_3$): δ 23.0, 26.6, 33.0, 42.1, 42.8, 45.4, 55.9, 78.3, 109.6, 111.1, 111.3, 113.0, 116.3, 124.6, 125.3, 125.5, 127.4 (2×C), 127.5, 128.5 (2×C), 137.7, 139.8, 141.3, 142.4, 156.0, 158.2, 169.5 (C=O). IR (KBr), ν (cm$^{-1}$): 3377 (N—H), 3029, 2975, 1676 (C=O), 1517, 1496, 1340, 1262, 1086, 909.

Photochromic properties of target compounds 6a,b and 7 were determined from solutions in acetonitrile (10$^{-5}$ M/L). Steady state UV-Vis absorption spectra were recorded on scanning spectrometer (Shimadzu UV-3101PC). Flash photolysis experiments were performed with Nd:YAG laser 3-rd harmonic radiation (EKSPLA NL30, pulse energy 3 mJ per impulse, λ=355 nm, pulse duration 5 ns). Number of pulses was determinated counting pulses, while maximum in the light absorption spectrum of opened form reached 0.8 of initial absorption maximum. A solution of benzophenone (0.5 OD at 355 nm) in MeCN, optically adjusted for wavelength of excitation, was used to measure quantum yields. Quantum yield of photochromic transition to opened form was evaluated comparing with control solution according to energetic characteristics (the growth of difference absorbance signal vs exciting pulse energy) and molar extinction coefficient.

Results of the measurements are provided in the Table.

| Compound | Structural formula | Absorption maximum in the visible spectrum of opened form, $\lambda_{max}$ (nm) | Characteristic relaxation time, T (ns) | Number of pulses $\Delta A/\Delta A_0 = 0,8$ | Quantum yield, $\varphi$ (%) |
|---|---|---|---|---|---|
| A | | 440 | 22 | 4000 | 5, 5 |
| 6a | | 490 | <5 | 17000 | 2, 7 |
| 6b | | 470 | <5 | 7000 | 3, 6 |
| 7 | | 490 | <5 | 5000 | 2, 2 |

The data on photochromic properties presented in the Table show that compounds of present invention can be used as molecular photoswitches, in which under UV radiation opening of 3,4-dihydro-2H-pyran ring occurs and coloured form of compound is generated, with subsequent thermal return to initial non-coloured form. The total duration of formation of coloured form and returning back to non-coloured form is less than 5 ns. The process is repeatable many times. Compounds of the present invention are characterized with high photostability without noticable degradation while operating more than 5000 cycles.

Compounds of the present invention are less sensitive to alkaline medium, than earlier mentioned compound A. If to a solution of analogue A in acetonitrile we will drop sodium hydroxide solution, immediately hydroxide ion will attack α-C carbon atom, 3,4-dihydropyrane ring will be opened and coloured nitrophenolate forms.

Figure 1:
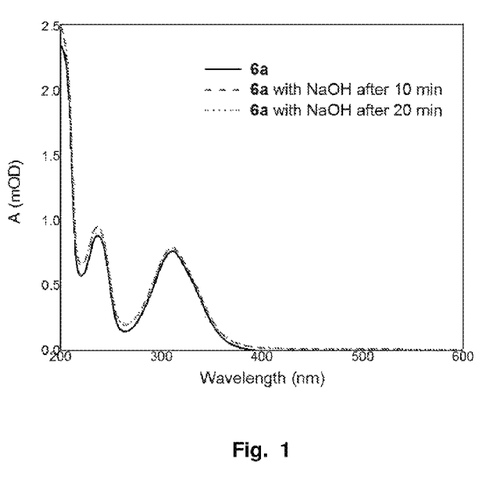
FIG. 1 shows kinetic spectra of compound 6a in acetonitrile after addition of NaOH (1 mMol NaOH)
Figure 2:
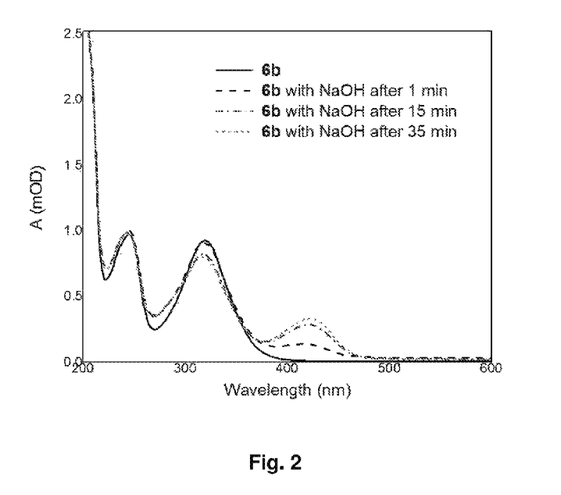
FIG. 2 shows kinetic spectra of compound 6b in acetonitrile after addition of NaOH (1 mMol NaOH)

Meanwhile spectra provided in FIG. 1 show that after treatment of compound 6a with sodium hydroxide, 3,4-dihydropyrane cycle remains stable and coloured 4-nitrophenolate anion does not form. Compound 6b (FIG. 2) is more sensitive to alkaline medium, but not so sensitive like compound A. Kinetic UV-Vis spectra of compound 6b are provided in FIG. 2.

In general, the present invention has the following main advantages comparing with the known state of the art:

1. The total duration of coloured form formation and returning back to the initial non-coloured state of cis- and trans-methanobenz[f][1,3]oxazepino[3,2-a]indoles of present invention is significantly shorter than in indolino spiropyrans or 1',3,3',4-tetrahydrospiro[chromen-2,2'-indoles].

2. cis-Methanobenz[f][1,3]oxazepino[3,2-a]indoles are characterized with pecular resistance to changes of medium, and coloured form appears only by action of UV radiation. Alkalies do not open [1,3]benzoxazine ring easily and do not generate coloured 4-nitrophenol fragment.

3. Compounds of the invention are characterized with higher resistance to photodestruction than 1',3,3',4-tetrahydrospiro[chromen-2,2'-indoles] and withstand more than 5000 opening-closing cycles.

4. These compounds are non-sensitive to the oxygen in the air and can be used in environment from which oxygen is not removed.

The invention claimed is:

1. Compounds of a general formula (I) or (II)

wherein $R^1$ and $R^2$ each independently is $C_1$-$C_3$ alkyl or $R^1$ and $R^2$ together are forming $(CH_2)_4$—; —$(CH_2)_5$—; $R^3$ is $C_1$-$C_6$ alkyl, benzyl, phenyl, allyl.

2. The compounds of the general formula (I) or (II) according to claim 1, wherein $R^1$ is methyl, $R^2$ is methyl, and $R^3$ is ethyl or benzyl.

3. The compound according to claim 1, which is (5aR*, 12R*,13S*)-N-ethyl-6,6,8-trimethyl-2-nitro-12,13-dihydro-6H-5a,13-methanoindolo[2,1-b][1,3]benzoxazepine-12-carboxamide (6a).

4. The compound according to claim 1, which is (5aR*, 12S*,13S*)-N-ethyl-6,6,8-trimethyl-2-nitro-12,13-dihydro-6H-5a,13-methanoindolo[2,1-b][1,3]benzoxazepin-12-carboxamide (7).

5. The compound according to claim 1, which is (5aR*, 12S*,13S*)-(N-benzyl-6,6,8-trim ethyl-2-n itro-12,13-dihydro-6H-5a,13-methanoindolo[2,1-b][1,3]benzoxazepin-12-carboxamide (6b).

6. The compound according to claim 1, which is exhibiting photochromic properties with characteristic relaxation time of less than 5 ns.

7. A method of using the compounds according to claim 1 comprising using said compounds as molecular photoswitches.

8. Compounds of a general formula (5), wherein $R^3$ is ethyl or benzyl.

9. Compounds of a general formula (4), wherein $R^3$ is ethyl or benzyl.

10. 7-Methoxy-9,9,9a-trimethyl-9,9a-dihydro-1H-imidazo[1,2-a]indol-2(3H)-one of a formula (3), 11. 1-Carbamoylmethyl-5-methoxy-2,3,3-trimethyl[3H] indolium chloride of a formula (2), 12. The compound according to claim 2, which is (5aR*, 12R*,13S*)-N-ethyl-6,6,8-trimethyl-2-nitro-12,13-dihydro-6H-5a,13-methanoindolo[2,1-b][1,3]benzoxazepine-12-carboxamide (6a).

13. The compound according to claim 2, which is (5aR*, 12S*,13S*)-N-ethyl-6,6,8-trimethyl-2-nitro-12,13-dihydro-6H-5a,13-methanoindolo[2,1-b][1,3]benzoxazepin-12-carboxamide (7).

14. The compound according to claim 2, which is (5aR*, 12S*,13S*)-(N-benzyl-6,6,8-trimethyl-2-nitro-12,13-dihydro-6H-5a,13-methanoindolo[2,1-b][1,3]benzoxazepin-12-carboxamide (6b).

15. The compound according to claim 2, which is exhibiting photochromic properties with characteristic relaxation time of less than 5 ns.

16. The compound according to claim 3, which is exhibiting photochromic properties with characteristic relaxation time of less than 5 ns.

17. The compound according to claim 12, which is exhibiting photochromic properties with characteristic relaxation time of less than 5 ns.

18. The compound according to claim 4, which is exhibiting photochromic properties with characteristic relaxation time of less than 5 ns.

19. The compound according to claim 13, which is exhibiting photochromic properties with characteristic relaxation time of less than 5 ns.

20. The compound according to claim 5, which is exhibiting photochromic properties with characteristic relaxation time of less than 5 ns.

\* \* \* \* \*